United States Patent [19]

Lyons

[11] Patent Number: 4,485,246

[45] Date of Patent: Nov. 27, 1984

[54] AMINE PROMOTED CATALYTIC HYDROGENATION OF CARBOXYLIC ACID ANHYDRIDES TO LACTONES OR ESTERS

[75] Inventor: James E. Lyons, Wallingford, Pa.

[73] Assignee: Sun Tech, Inc., Philadelphia, Pa.

[21] Appl. No.: 437,725

[22] Filed: Oct. 29, 1982

[51] Int. Cl.³ .................. C07D 307/20; C07D 307/83
[52] U.S. Cl. .................................... 549/302; 549/307; 549/311; 549/325; 560/1; 560/106; 560/122; 560/265
[58] Field of Search ............... 549/325, 302, 307, 273, 549/311; 560/265, 106, 1, 122

[56] References Cited

U.S. PATENT DOCUMENTS 3,957,827  5/1976  Lyons .................................. 549/325

Primary Examiner—Jane T. Fan
Attorney, Agent, or Firm—J. Edward Hess; Donald R. Johnson; Stanford M. Back

[57] ABSTRACT

The rate of selective hydrogenation of carboxylic acid anhydrides to esters or lactones in the presence of a ruthenium organophosphorous catalyst which contains or liberates a hydrogen halide during the hydrogenation, is improved by providing in the reaction medium prior to or during the hydrogenation a basic amino compound to remove the hydrogen halide.

12 Claims, No Drawings

AMINE PROMOTED CATALYTIC HYDROGENATION OF CARBOXYLIC ACID ANHYDRIDES TO LACTONES OR ESTERS

BACKGROUND OF THE INVENTION

This invention relates to an improved process for catalytically hydrogenating acyclic and cyclic carboxylic acid anhydrides to esters and lactones, respectively, wherein the catalyst is a ruthenium organophosphorous complex.

U.S. Pat. No. 3,957,827 to J. E. Lyons, issued May 18, 1976, describes the selective catalytic hydrogenation of acyclic and cyclic carboxylic acid anhydrides to esters and lactones wherein the catalyst is a ruthenium organophosphorus complex of the formula (I):

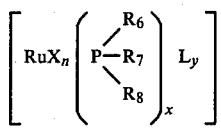

where X is hydrogen, chlorine, bromine, iodine or lower alkyl; n is an integer of from 0 to 2, but when n is 2, X may be the same or different; L is a neutral ligand, olefin or CO; y is an integer of from 0 to 3, but when y is 2 or 3, L may be the same or different; $R_6$, $R_7$ and $R_8$ are lower alkyl, cycloalkyl of from 5 to 15 carbon atoms, aryl, benzyl or a bidentate ligand, and each of the R groups may be the same or different; and x is an integer of from 1 to 3. The reaction occurs readily under mild reaction conditions in homogeneous solution and is characterized by good selectivity and yield, and does not proceed beyond ester or lactone formation.

When X in formula I is a hydrogen halide such as HCl or dihalide such as $Cl_2$, or when the catalyst of formula I is formed in situ in the reaction mixture such that a hydrogen halide or a dihalide remains in the reaction mixture, the hydrogen halide contained in the reaction mixture or liberated during the hydrogenation reaction can catalyze hydrolysis of starting carboxylic acid anhydride to the corresponding acid. This hydrolysis reaction thus competes with production of the ester or lactone.

Additional competition results from formation of water as a byproduct of the hydrogenation, since the water also promotes hydrolysis of starting anhydride to the acid form. The effect of the latter hydrolysis reaction can be minimized or somewhat offset by the addition of water scavengers such as a molecular sieve or $MgSO_4$, in combination with recovery, dehydration and recycling of any acid which neverless may form. However, the catalytic hydrolysis effected by the hydrogen halide will persist.

A similar problem occurs in the hydrogenation reaction with an improved version of the ruthenium organophosphorus catalyst, which hydrogenation reaction and catalyst are described in the copending application of Chao-Yang Hsu and James E. Lyons entitled "Hydrogenation of Carboxylic Acid Anhydrides to Lactones or Esters Using a Ruthenium Trichlorostannate Catalyst," which application is filed simultaneously with the present application and is incorporated herein by reference. However, in the improved process of the copending application the catalyst is more active than the catalyst of U.S. Pat. No. 3,957,827, thereby favoring the hydrogenation reaction over the competing hydrolysis. The catalyst of the copending application has the following formula (II):

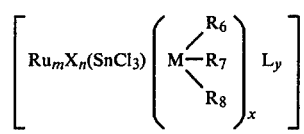

wherein X is hydrogen, chlorine, bromine, iodine or lower alkyl; m is the integer 1 or 2; n is an integer of from 0 to 3 but when n is 2 or 3, X may be the same or different; M is P, As or Sb; $R^6$, $R^7$ and $R^8$ independently are lower alkyl, cycloalkyl, aryl, benzyl or a bidentate ligand; x is an integer of from 1 to 4 but when x is 2 or more, M may be the same or different; L is a neutral ligand, olefin, CO or $(R^9)_2CO$ wherein $R^9$ is lower alkyl; y is an integer of from 0 to 3 but when y is 2 or 3, L may be the same or different; and the sum of x and y is at least 2.

As in the case of the ruthenium catalyst of U.S. Pat. No. 3,957,827 the source of the hydrogen halide hydrolysis catalyst can be either those forms of the ruthenium catalyst which can liberate the hydrogen halide during the hydrogenation reaction or can be free hydrogen halide in the catalyst when the catalyst is formed in situ in the reaction mixture.

SUMMARY OF THE INVENTION

In accordance with the present invention the competing hydrolysis reaction occurring simultaneously with hydrogenation of acyclic and cyclic carboxylic acid anhydrides to esters or lactones, which is catalyzed by the presence of hydrogen halide in the hydrogenation reaction product mixture, can be avoided or minimized by the presence of a basic amino compound in the hydrogenation reaction mixture.

The amino compound influences the hydrogenation reaction in several ways. In addition to removing the hydrogen halide, thereby eliminating the catalytic driving force for the undesired hydrolysis reaction, the amino compound also increases the rate of formation of the ruthenium hydride species from the ruthenium organophosphorus complex, which species is believed to be primarily responsible for catalyzing the desired hydrogenation reaction. Moreover, removal of hydrogen halide byproduct, a highly corrosive agent, also eliminates this source of corrosion. The cumulative effect, therefore, of the amino compound is increased hydrogenation and reduced hydrolysis, with resultant higher yields of ester or lactone.

DETAILED DESCRIPTION

Generally, the hydrogenation reaction promoted by the amino compounds in accordance with the present invention proceeds as in U.S. Pat. No. 3,957,827 as summarized below in equations 1 and 2:

Acyclic acid anhydride to ester:

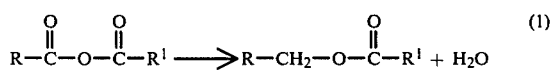

wherein R and $R^1$ independently are lower alkyl (for example, from 1 to 8 carbon atoms), cycloalkyl (for example, from 5 to 15 carbon atoms) or aryl.

Cyclic acid anhydride to lactone:

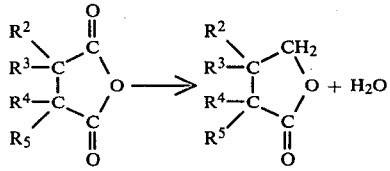
(2)

wherein $R^2$, $R^3$, $R^4$ and $R^5$ independently are hydrogen, lower alkyl, cycloakyl or aryl; and wherein the R groups taken together may form a saturated or unsaturated ring having, for example, from 5 to 8 carbon atoms, or an aromatic ring, both monocyclic and condensed.

The reaction proceeds in homogeneous solution under mild conditions of temperature and pressure, e.g., about 50°–150° C., preferably 90°–110° C., and about 40–400 psi hydrogen, preferably 100–150 psi. Higher hydrogen pressures favor faster rates of hydrogenation. Conventional solvents for homogeneous catalytic reactions are employed, such as benzene or toluene.

Typical ruthenium catalysts of formula I useful in this invention are the following, the preparation of which are described in U.S. Pat. No. 3,957,827:

$RuCl_2(PPh_3)_3$
$RuHCl(PPH_3)_3$
$RuCl_2(CO)(PPh_3)_3(C_3H_{12})$
$RuBr_2(PPH_3)_3$
$RuHBr(PPh_3)_3$
$RuCl_2(PPh_2CH_2)_3$

The ruthenium catalysts of formula II useful in this invention include the following:

$[RuCl(SnCl_3)(PPh_3)_2]$
$[Ru_2Cl_3(SnCl_3)(CO)_2(PPh_3)_4]$
$[Ru_2Cl_3(SnCl_3)(CO)_2(PPh_3)_2(Me_2CO)_2]$
$[RuH(SnCl_3)(PPh_3)_3]$
$[RuCl(SnCl_3)(P\ tolyl_3)_3]$
$[RuCl(SnCl_3)(P\ cyclohexyl_3)_3]$
$[RuCl(SnCl_3)(DIPHOS)]$
$[RuCl(SnCl_3)(ARPHOS)]$ wherein Ph is phenyl, Me is methyl, DIPHOS is $(PPh_3)_2$ and ARPHOS is $AsPh_3PPh_3$. Preferably, in formula II, when m is 1, n is also 1 and $x+y$ is 3. When m is 2, n preferably is 3 and $x+y$ is from 5 to 8. Typical L groups are CO, $(CH_3)_2CO$, ketone, lactone, ether, $(R^{10})_3As$ and $(R^{10})_3N$ where $R^{10}$ is a hydrocarbon group such as lower alkyl (e.g., $C_1$–$C_8$) or cyclic alkyl (e.g., $C_5$–$C_{15}$). The L groups may be the same or different.

While the catalysts of formula II include those complexes resulting from substitution of $SnCl_3$ for one of the X groups in the complexes of formula I, it will be evident that a variety of other compounds are additionally encompassed by formula II. Moreover, anionic and salt forms of the complexes are suitable, depending on the extent to which such electrolytes are compatible with other components of the homogeneous reaction medium.

The complexes of formula II are prepared as described by Stephenson and Wilkinson, J. Inorg. Nucl. Chem. 28 (1966) 945–956 and by Antonov et al, Khim. Khim. Tekhnol., 1981, 24 (6), 663–665 (abstracted in Platinum Metals Review, 26(1), Jan. 1982, page 44).

The catalysts may also be generated in situ during or prior to the hydrogenation process by introducing $SnCl_2$ as a powder or solvent solution, preferably in molar excess, into a reaction mixture of the starting anhydride, precursor complex of formula I (or other precursor such as described in the above article by Stephenson and Wilkinson) and solvent medium. Alternatively the $SnCl_2$ may be added before or during introduction of the anhydride.

The amino compounds used to promote the hydrogenation reactions of equations 1 and 2 are organic amines, both low molecular weight compounds and polymers, which are sufficiently basic for reaction with the hydrogen halide in the reaction medium. While the more basic aliphatic and cycloaliphatic, saturated or unsaturated, monoamines are preferred for reasons of economy and ease of handling in the hydrogenation reaction (e.g., liquid state, low volatility and good miscibility in the reaction medium), aromatic and N-heterocyclic amino compounds and even amino compounds containing other functionality (such as oxygen or sulfur atoms) can be used, provided such other atoms or groups are not so electron withdrawing as to void the electron donating power of the electron pair on the nitrogen atom. In addition to giving attention to an effective level of basicity, one skilled in the art will appreciate, when selecting the amino compounds, that from the standpoint of reactivity towards hydrogen halide, sterically hindered amines normally are less desirable than amines having small groups on the nitrogen atom, and that those amino compounds which may saturate the coordination sphere of the ruthenium catalyst (thus destroying the catalyst properties) are to be avoided. Pyridine is believed to have this destructive character although it is basic.

As is generally known, the basicity of alkylamines decreases in the order: tertiary amine, secondary amine, primary amine. Accordingly, the more desirable amines are tertiary alkyl monoamines such as trimethylamine, triethylamine, tripropylamine, N-ethyl-N-methylpropylamine, N,N-dimethylbutylane, N-ethyldipropylamine, and similar alkyl, cycloalkyl or aralkyl amines of the formula $R_3N$ where the R groups taken together total from 3 to about 20 carbon atoms and the R groups may be the same or different. Secondary amines include diethylamine, dipropylamine, N-propylallylamine, N-cyclohexylhexylamine, N-phenylbenzylamine, and the like. Primary amines include n-butylamine, cyclohexylamine, n-octylamine, n-decylamine, benzylamine, phenethylamine, and the like. Among the useful N-heterocyclic amines may be mentioned quinoline, piperidrine, picoline, indole, and the like, including isomers thereof. The polyamines include both the alkylene polyamines and polyamino compounds containing alicylic or aromatic groups, such as 1,2-propanediamine, diethylenetriamine, triethylenetriamine, 1,4-naphthylene diamine and the like.

Moreover, although amines which are liquids under the hydrogenation reaction conditions are preferred, basic polymeric amines which are in solid particulate form (such as beads) are also useful. Typical of such amino compounds are the well-known weakly or strongly basic ion exchange resins. The former are represented by styrene-divinylbenzene copolymers which are chlorinated or chloromethylated and then functionalized with a primary or secondary alkylamine such as diethylamine, or other amine. The strongly basic ion exchange resins are represented by styrene-divinylbenzene copolymers containing chloro or chloromethyl groups which are functionalized with tertiary amines to form quaternary amino groups on the copolymers. Typical patents describing such resins are U.S. Pat. Nos. 4,191,814, 4,192,920 and 4,207,399. Both gel and macroreticular resins are useful.

The amine promoters may be added to the reaction mixture at any time before or during the hydrogenation process but preferably are present in the reaction mixture prior to the hydrogenation. They can be added with the ruthenium catalyst, ahead of the catalyst or with the catalyst precursors if the catalyst is prepared in situ in the reaction mixture, provided that in the case of catalysts of formula II, the tin halide complexes with the ruthenium before the amino compound is added. Preferably the amino compound is added to the preformed catalyst solution, which is then added to the reaction solution. About 0.5 to 10 moles of the amino compound per mole of catalyst, preferably about 1–3 moles per mole catalyst, will be effective but greater or lesser proportions may be acceptable depending on the specific catalyst and hydrogenation conditions.

Workup, including separation of product, catalyst and amine salt, and other aspects of the hydrogenation process are essentially the same as in U.S. Pat. No. 3,957,827 and the copending application referred to above which discloses a hydrogenation process using the improved catalyst of formula II. Moreover, dehydration can be practiced as in U.S. Pat. No. 3,957,827 in order to minimize or offset hydrolysis of the starting anhydride. Dehydrating agents include molecular sieves, $MgSO_4$, and organic compounds such as ketals and acetals (e.g., 2,2-dimethoxypropane, methylal, 1,1-dimethoxycyclohexane, and the like), and orthoformates (e.g., methylorthoformate, ethylorthoformate, and the like).

The following examples further illustrate the invention.

EXAMPLE 1

Succinic anhydride, 2.0 grams, toluene, 4.0 ml, [$RuCl_2(Ph_3P)_3$], 0.1 gram, and triethylamine 0.02 gram, are stirred at 100° C. under 150 psi hydrogen. During the reaction the anhydride slowly dissolves to form a solution which absorbs hydrogen steadily. After hydrogen absorption has stopped, the mixture is allowed to stir for an additional two hours under 150 psi hydrogen and 100° C. The mixture is cooled to precipitate amine hydrochloride and acid formed during the reaction. Remaining in the solution is gamma-butyrolactone which is formed in good yield.

EXAMPLE 2

Substantially as described in Example 1 but substituting phthalic anhydride for succinic anhydride, phthalide is generated in good yield.

EXAMPLE 3

Substantially as described in Example 1 but substituting [$RuCl(SnCl_3)(PPh_3)_2$] for the [$RuCl_2(Ph_3P)_3$] catalyst, and substituting phthalic anhydride for succinic anhydride, a good yield of phthalide is obtained.

I claim:

1. In a process for hydrogenating, in homogeneous reaction solution at elevated temperature and pressure, acyclic and cyclic carboxylic acid anhydrides to form esters or lactones in the presence of a ruthenium organophosphorus catalyst which contains or liberates a hydrogen halide during hydrogenation, the improvement which comprises providing in the reaction solution prior to or during the hydrogenation a basic organic amino compound which is non-destructive of the ruthenium organophosphorus catalyst, in an amount effective to react with the hydrogen halide which may form, whereby the rate of hydrogenation is increased; and wherein the carboxylic acid anhydrides are selected from

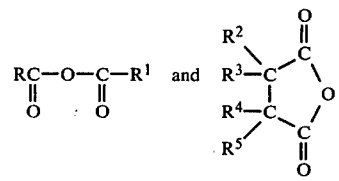

to form the ester $$R-CH_2-O-\underset{\underset{O}{\|}}{C}-R^1$$

and the lactone

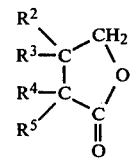

respectively, wherein R and $R^1$ independently are lower alkyl or cycloalkyl ($C_5$–$C_{15}$); $R^2$, $R^3$, $R^4$ and $R^5$ independently are hydrogen, lower alkyl, cycloalkyl ($C_5$–$C_{15}$) or aryl; and wherein $R_3$ and $R_4$ taken together may form a saturated or unsaturated ring, or an aromatic ring.

2. The process of claim 1 wherein the amino compound is an aliphatic or cycloaliphatic monoamine, an aromatic amine, an N-heterocyclic amine, an alkylene polyamine, or a basic ion exchange resin.

3. The process of claim 1 wherein the amino compound is an alkylamine containing 3 to about 20 carbon atoms.

4. The process of claim 3 wherein the alkylamine is a secondary or tertiary amine.

5. The process of claim 1 wherein the amino compound is triethylamine.

6. The process of claim 1 wherein the amino compound is added to the reaction solution prior to the hydrogenation.

7. The process of claim 1 wherein the ruthenium organophosphorus catalyst is generated in situ in the reaction solution, and the amino compound is added to the reaction solution after addition of the catalyst precursors and before hydrogenation.

8. The process of claim 1 wherein the ruthenium catalyst is prepared as a catalyst solution prior to addition to the reaction solution, and the amino compound is added to the reaction solution with the catalyst solution.

9. The process of claim 8 wherein the amino compound is a secondary or tertiary alkylamine containing 3 to about 20 carbon atoms.

10. The process of claim 8 wherein the amino compound is triethylamine.

11. The process of claim 1 wherein the carboxylic acid anhydride starting material is phthalic anhydride and the lactone product is phthalide.

12. The process of claim 1 wherein the carboxylic acid anhydride starting material is succinic anhydride and the lactone product is gamma butyrolactone.

* * * * *